(12) United States Patent
Schabbach et al.

(10) Patent No.: US 11,311,675 B2
(45) Date of Patent: Apr. 26, 2022

(54) MEDICAMENT DELIVERY DEVICE

(71) Applicant: SANOFI-AVENTIS DEUTSCHLAND GMBH, Frankfurt am Main (DE)

(72) Inventors: Michael Schabbach, Frankfurt am Main (DE); Beate Franke, Frankfurt am Main (DE); Andrew Nelson, Dallas, TX (US); Giuliano Pradel, Besana in Brianza (IT)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 476 days.

(21) Appl. No.: 16/324,818

(22) PCT Filed: Aug. 9, 2017

(86) PCT No.: PCT/EP2017/070154
§ 371 (c)(1),
(2) Date: Feb. 11, 2019

(87) PCT Pub. No.: WO2018/029238
PCT Pub. Date: Feb. 15, 2018

(65) Prior Publication Data
US 2019/0175840 A1 Jun. 13, 2019

(30) Foreign Application Priority Data
Aug. 12, 2016 (EP) .................................. 16184073

(51) Int. Cl.
*A61M 5/315* (2006.01)
*A61M 5/142* (2006.01)
(Continued)

(52) U.S. Cl.
CPC ........ *A61M 5/31515* (2013.01); *A61M 5/142* (2013.01); *A61M 5/2033* (2013.01);
(Continued)

(58) Field of Classification Search
CPC ............. A61M 5/31515; A61M 5/142; A61M 5/2033; A61M 5/2459; A61M 5/3158;
(Continued)

(56) References Cited

U.S. PATENT DOCUMENTS 6,149,626 A * 11/2000 Bachynsky ......... A61M 5/2033
604/134
2013/0110049 A1 5/2013 Cronenberg et al.
(Continued)

FOREIGN PATENT DOCUMENTS

CN 1753699 3/2006
CN 201529296 7/2010
(Continued)

OTHER PUBLICATIONS

Zhou et al., "Needle-free Injection Administration System and Application thereof", Pharmaceutical Journal of Chinese People's Liberation Army, Dec. 2005, 21(6):439-443 (With Machine Translation of Abstract).
(Continued)

*Primary Examiner* — James D Ponton
(74) *Attorney, Agent, or Firm* — Fish & Richardson P.C.

(57) ABSTRACT

The present disclosure relates to a medicament delivery device. The medicament delivery device includes a needle for delivering a medicament and an insertion mechanism configured to urge the needle in a first direction parallel to a longitudinal axis of the needle. The insertion mechanism includes a driving mechanism and a cam. The driving mechanism is configured to exert a force in a second direction perpendicular to the first direction. The cam is coupled to the needle and is configured to receive a force from the driving mechanism and move in the first direction in response to the received force.

11 Claims, 7 Drawing Sheets

(51) Int. Cl.
*A61M 5/20* (2006.01)
*A61M 5/24* (2006.01)
*A61M 5/158* (2006.01)
*A61M 5/145* (2006.01)

(52) U.S. Cl.
CPC ........ *A61M 5/2459* (2013.01); *A61M 5/3158* (2013.01); *A61M 5/1454* (2013.01); *A61M 5/14526* (2013.01); *A61M 2005/14252* (2013.01); *A61M 2005/14533* (2013.01); *A61M 2005/1581* (2013.01); *A61M 2005/206* (2013.01); *A61M 2005/2073* (2013.01); *A61M 2005/2086* (2013.01); *A61M 2205/8206* (2013.01)

(58) Field of Classification Search
CPC ............ A61M 5/14256; A61M 5/1454; A61M 2005/14252; A61M 2005/14533; A61M 2005/1581; A61M 2005/206; A61M 2005/2073; A61M 2005/2086; A61M 2205/8206
See application file for complete search history.

(56) References Cited

U.S. PATENT DOCUMENTS

| | | | |
|---|---|---|---|
| 2013/0172695 A1 | 7/2013 | Nielsen et al. | |
| 2014/0207104 A1* | 7/2014 | Vouillamoz | A61M 5/14248 604/506 |
| 2015/0174317 A1 | 6/2015 | Momose | |
| 2015/0182697 A1 | 7/2015 | Panzer | |
| 2015/0374926 A1 | 12/2015 | Gross et al. | |
| 2016/0121043 A1 | 5/2016 | Weibel | |
| 2017/0354788 A1* | 12/2017 | Quinn | A61M 5/14248 |

FOREIGN PATENT DOCUMENTS

| | | |
|---|---|---|
| CN | 102325559 | 1/2012 |
| CN | 103458941 | 12/2013 |
| CN | 103857427 | 6/2014 |
| CN | 203898932 | 10/2014 |
| CN | 104245022 | 12/2014 |
| CN | 104321093 | 1/2015 |
| CN | 104474604 | 4/2015 |
| CN | 104721903 | 6/2015 |
| CN | 104984438 | 10/2015 |
| CN | 105492037 | 4/2016 |
| CN | 105517593 | 4/2016 |
| CN | 105597198 | 5/2016 |
| JP | 2006-122572 | 5/2006 |
| JP | 2014-510571 | 5/2014 |
| JP | 2014-521443 | 8/2014 |
| JP | 2016-523123 | 8/2016 |
| WO | WO 2004/058332 | 7/2004 |
| WO | WO 2009/103759 | 8/2009 |
| WO | WO 2010/070038 | 6/2010 |
| WO | WO 2010/077279 | 7/2010 |
| WO | WO 2011/046950 | 4/2011 |
| WO | WO 2012/108955 | 8/2012 |
| WO | WO 2012/139878 | 10/2012 |
| WO | WO 2013/016376 | 1/2013 |
| WO | WO 2013/078200 | 5/2013 |
| WO | WO 2013/114221 | 8/2013 |
| WO | WO 2013/148270 | 10/2013 |
| WO | WO 2014/191038 | 12/2014 |
| WO | WO 2014/194183 | 12/2014 |
| WO | WO 2015/032740 | 3/2015 |

OTHER PUBLICATIONS

International Search Report and Written Opinion in Application No. PCT/EP2017/070154, dated Nov. 7, 2017, 8 pages.
International Preliminary Report on Patentability in Application No. PCT/EP2017/070154, dated Feb. 12, 2019, 7 pages.
Lai, "Practice of mould design and manufacturing technology", Movable Wedge (Wedge Moving Mechanism), Apr. 1979, pp. 136-141 and Figures 421-427 (with Machine translation).

* cited by examiner

MEDICAMENT DELIVERY DEVICE

CROSS REFERENCE TO RELATED APPLICATIONS

The present application is the national stage entry of International Patent Application No. PCT/EP2017/070154, filed on Aug. 9, 2017, and claims priority to Application No. EP 16184073.1, filed on Aug. 12, 2016, the disclosures of which are incorporated herein by reference.

FIELD OF INVENTION

The present disclosure relates to a device for delivery of medicament to a patient.

BACKGROUND

A variety of diseases exist that require regular treatment by injection of a medicament and such injections can be performed by using injection devices. Injection or infusion pumps of the type known as patch pumps for delivering injections of medicament are known in the art. Another type of injection pump that is gaining traction is the bolus injector device. Some bolus injector devices are intended to be used with relatively large volumes of medicament, typically at least 1 ml and maybe a few ml. Injection of such large volumes of medicament can take some minutes or even hours. Such high capacity bolus injector devices can be called large volume devices (LVDs). Generally such devices are operated by the patients themselves, although they may also be operated by medical personnel.

To use a patch pump or bolus injector device, such as an LVD, it is first supported on a suitable injection site on a patient's skin. Once installed, injection is initiated by the patient or another person (user). Typically, the initiation is effected by the user operating an electrical switch, which causes a controller to operate the device. Operation includes firstly injecting a needle into the user and then causing the injection of medicament into the user's tissue. Biological medicaments are being increasingly developed which comprise higher viscosity injectable liquids and which are to be administered in larger volumes than long-known liquid medicaments. LVDs for administering such biological medicaments may comprise a pre-filled disposable drug delivery device or, alternatively, a disposable drug delivery device into which a patient or medical personnel must insert a drug cartridge prior to use.

SUMMARY

According to an aspect a medicament delivery device is provided including a needle for delivering a medicament; and an insertion mechanism configured to urge the needle in a first direction parallel to a longitudinal axis of the needle; wherein the insertion mechanism includes a driving mechanism which is configured to exert a force in a second direction perpendicular to the first direction, and a cam which is coupled to the needle and is configured to receive a force from the driving mechanism and move in the first direction in response to the received force.

The cam may include comprise an angled surface arranged at an angle between the first direction and the second direction and a guide configured to allow movement of the cam surface in the first direction only.

The driving mechanism may be configured to exert a force in the second direction on the angled surface of the cam.

The angled surface of the cam may be arranged at an angle between 20 degrees and 50 degrees with respect to the first direction.

The driving mechanism may include a driving plunger having an angled surface to make contact with the angled surface of the cam and exert a force on the cam.

The driving mechanism may include an insertion spring configured to expand in the second direction and push the driving plunger against the cam.

The driving mechanism may include an insertion spring latch; wherein in a first position, the insertion spring latch is arranged to prevent the insertion spring from expanding in the second direction; and in a second position, the insertion spring latch is arranged to allow the insertion spring to expand in the second direction.

The device may include a syringe for delivering a medicament through the needle; and an injection mechanism configured to urge a stopper of the syringe through a medicament chamber of the syringe.

The injection mechanism may include a syringe plunger arranged to make contact with the stopper, and an injection spring configured to expand and push against the syringe plunger to urge the stopper through the medicament chamber.

The injection mechanism may include an injection spring latch; wherein in a first position, the injection spring latch is arranged to prevent the injection spring from expanding; and in a second position, injection spring latch is arranged to allow the injection spring to expand and push against the syringe plunger.

The injection spring may be arranged coaxially within the insertion spring.

The injection spring, syringe plunger and injection spring latch may be arranged internally within the driving plunger.

The driving plunger may be arranged such that, on expansion of the insertion spring in the second direction, the syringe plunger is moved into contact with the stopper of the syringe.

The syringe may be configured to deliver a medicament through a flexible conduit, and the flexible conduit may be connected with an upper end of the needle.

The syringe may be configured to deliver a medicament through a flexible conduit, and the insertion mechanism may be configured to move the needle in the first direction from a first position to a second position.

The needle in the first position may be separated from the flexible conduit, and the needle in the second position may be arranged to engage with the flexible conduit.

The needle may include a piercing element, and the piercing element of the needle may be arranged to engage with a receiving portion of the flexible conduit in the second position.

The device may include a medicament for delivery through the needle.

These and other aspects of the disclosure will be apparent from and elucidated with reference to the embodiments described hereinafter.

BRIEF DESCRIPTION OF THE DRAWINGS

Exemplary embodiments of the present disclosure are described with reference to the accompanying drawings, in which.

DETAILED DESCRIPTION

Figure 1:
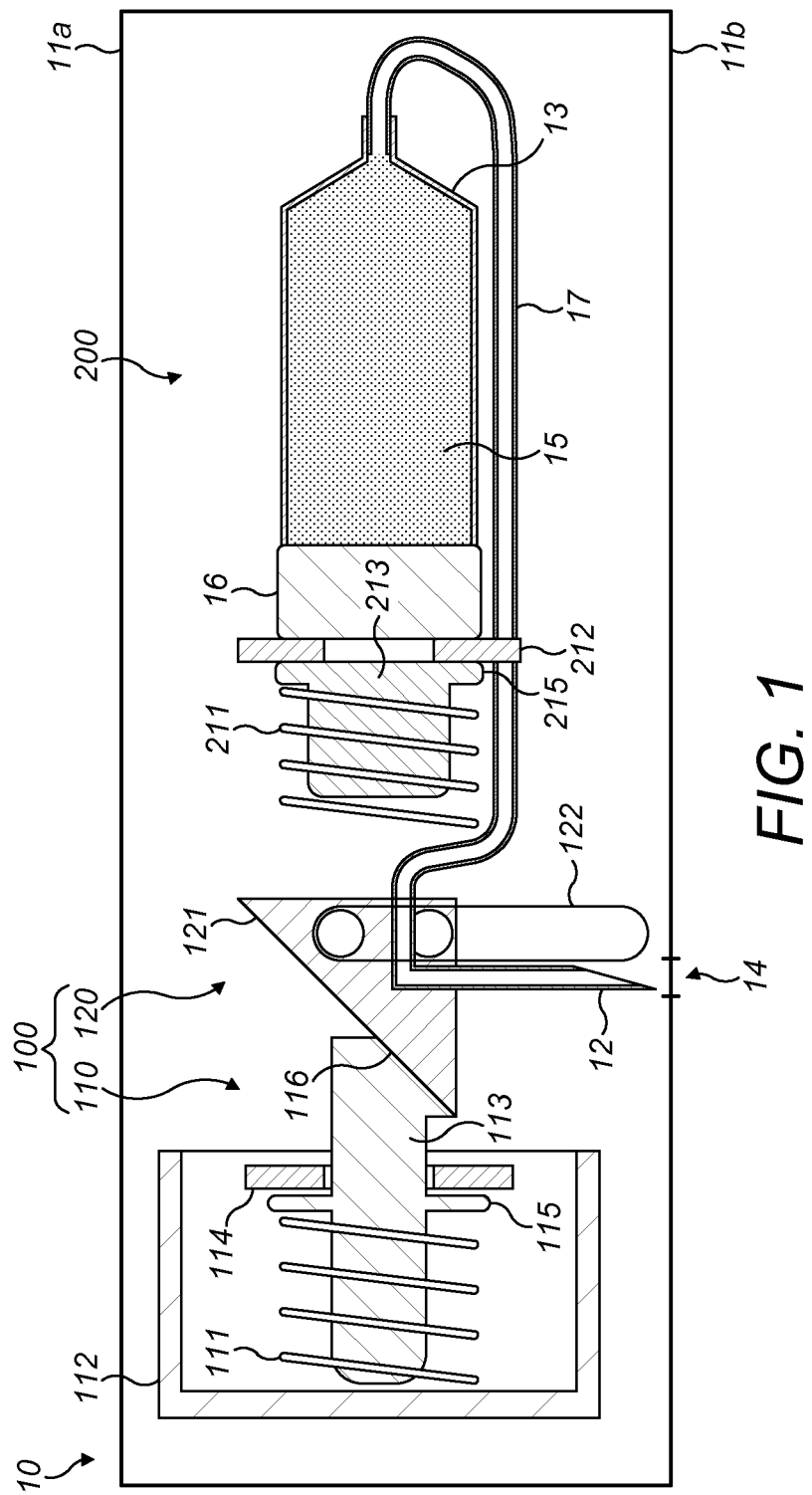
FIG. 1 is a schematic side view of a first embodiment of a medicament delivery device.

A medicament delivery device, as described herein, may be configured to inject a medicament into a patient. For example, delivery could be sub-cutaneous, intra-muscular, or intravenous. Such a device could be operated by a patient or by a care-giver, such as a nurse or physician. The device can include a cartridge-based system that requires piercing a sealed ampule before use. The device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g. about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The medicament delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of a device may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a trigger against their body in order to cause injection of a medicament. Other devices may require a multi-step activation of an automated function. For example, a user may be required to depress a button and deploy a needle in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some medicament delivery devices can also include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 2:
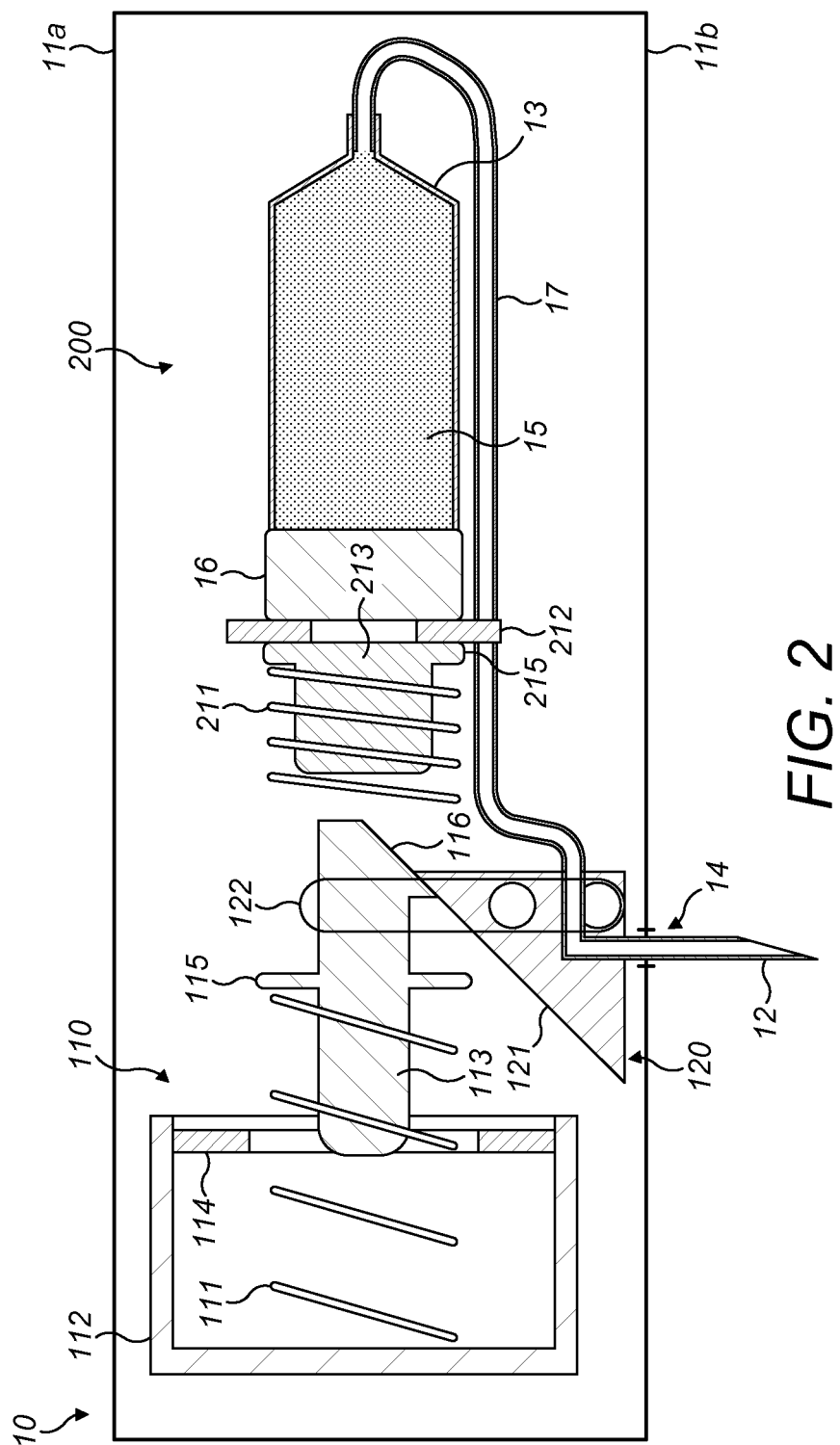
FIG. 2 is a schematic side view of the FIG. 1 injection device.
Figure 3:
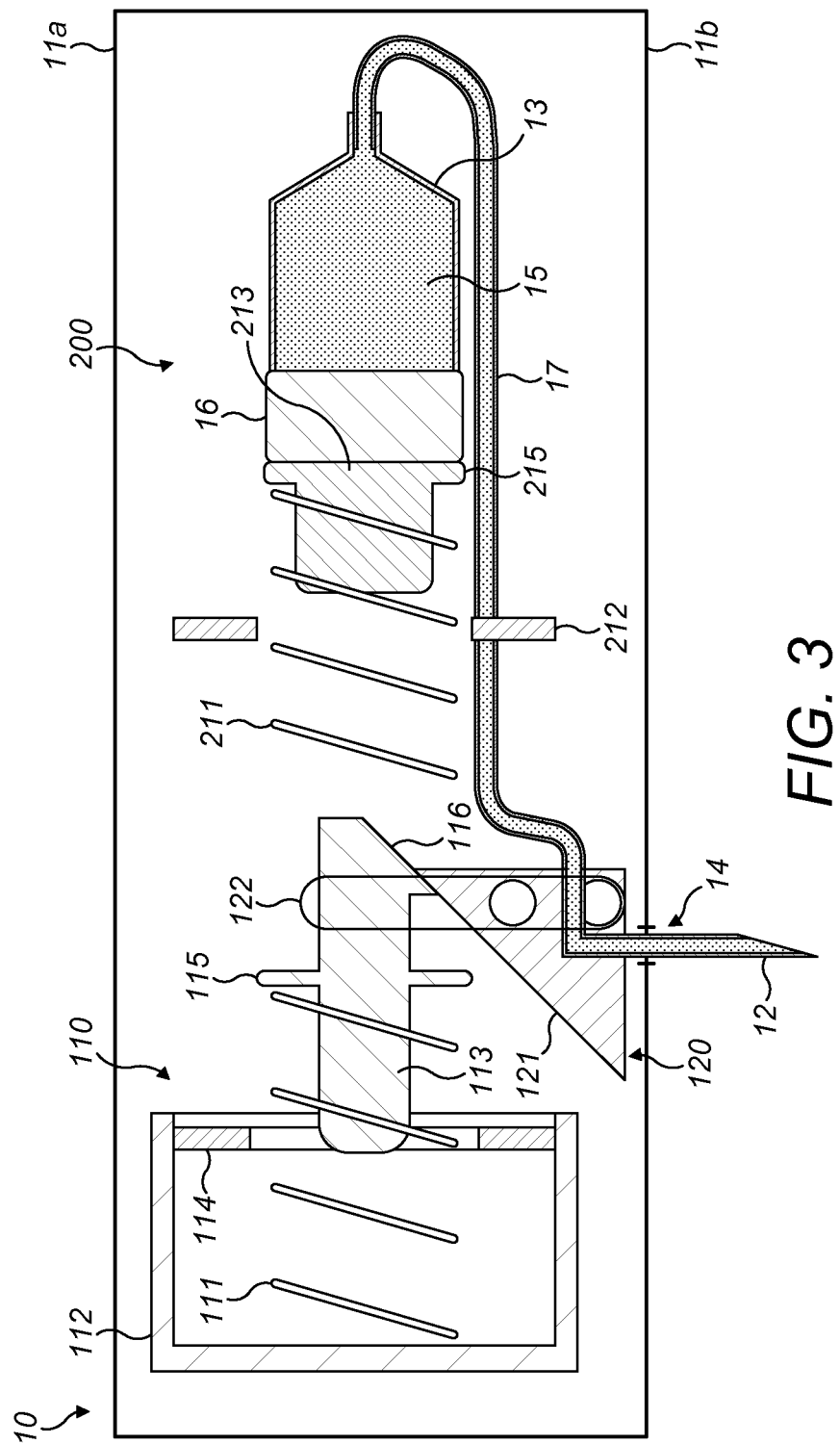
FIG. 3 is a schematic side view of the FIG. 1 injection device.

FIGS. 1 to 3 show a medicament delivery device 10, which in the exemplary embodiment comprises a bolus injector device (hereafter simply referred to as "device 10"), according to a first embodiment comprises a housing 11 containing a needle insertion mechanism 100 and a medicament injection mechanism 200. The device 10 can include an LVD. The device 10 is only shown schematically and a number of the functional components are omitted for the sake of clarity and brevity, but the device 10 includes a needle 12 for injection of the liquid medicament into a patient's body. The liquid medicament may be provided in a syringe 13 within the housing 11, or may be provided externally of the device 10.

Although not shown in the figures, the device 10 may include one or more of the following components. A controller configured to control operation of the device 10. An energy source to power the device 10. An electrical power source in the form of a battery to power to the controller. The battery may also provide electrical power to the insertion mechanism 100 and/or the injection mechanism 200, if this is an electrically driven device.

The device 10 generally comprises a housing upper side 11a and a lower side 11b. In use, the lower side 11b of the housing 11 is intended to be a contact surface that is placed against a patient's skin during a medicament administration process. The lower side 11b forms a flat contact surface. The lower side 11b may comprise an adhesive layer to removably adhere to a patient's skin. A height of the device 10, measured between the upper side 11a and the lower side 11b, may be short with respect to the size of the lower side 11b. A length of the lower side 11b may be greater than the height of the device 10. A width of the lower side 11b may be greater than the height of the device 10. The device 10 is stable when placed in position against a patient's skin.

The contact surface or lower side 11b of the housing 11 includes an aperture 14 through which the needle 12 can project in use. A length of needle 12 defines a first axis of the device 10. The first axis is perpendicular to the contact surface with a patient's skin when the lower side 11b is placed against the patient's skin. The height of the device 10 is measured along the first axis. A second axis of the device 10 is perpendicular to the first axis. The second axis is parallel to the lower side 11b of the housing 11.

The needle 12 is moveable along the first axis. The needle 12 can be moved between a retracted position and an engaged position. In the retracted position the needle 12 is disposed within the housing 11 of the device 10. In the engaged position, the needle 12 projects from the lower side 11b of the housing 11 through the aperture 14. The needle 12 is arranged in the engaged position so as to pierce and inject a patient's skin when the device 10 is in contact with a patient.

The needle insertion mechanism 100 is configured to move the needle 12 from the retracted position to the engaged position. The needle insertion mechanism 100 comprises a driving mechanism 110 to generate a motive force to move the needle 12. The needle insertion mechanism 100 comprises a cam 120 to translate the motive force of the driving mechanism 110 to a different axis.

The driving mechanism 110 comprises an insertion spring 111, a frame 112, a driving plunger 113 and an insertion spring latch 114. The insertion spring 111 is a compressible spring. The insertion spring may be, for example, an extended coil spring. In an initial state, the insertion spring 111 is fully compressed. In an activated state, the insertion spring 111 is fully extended. When activated, the insertion spring 111 is configured to expand. The insertion spring 111 is arranged to expand along the second axis of the device 10. The insertion spring 111 is arranged between the frame 112 and the driving plunger 113. The insertion spring 111 is arranged to push against the frame 112 and the driving plunger 113 when activated.

The frame 112 is a rectangular box. The box of the frame is open at one side. The frame 112 is arranged with the open face of the box facing along the second axis of the device 10. The inner face of the frame 112 which faces the opening is the rear face of the frame 112. The insertion spring 111 is arranged inside the frame 112. The insertion spring 111 is arranged in abutment with the rear face of the frame 112. The insertion spring 111 may be fixedly attached to the rear face of the frame 112. The insertion spring 111 may lie entirely within the frame 112 when fully compressed. The insertion spring 111 may extend through the open face of the frame 112 when fully expanded.

The rear face of the frame 112 forms a reaction surface against which the insertion spring 111 can push. The frame 112 is fixed in position within the housing of the device 10. The frame 112 is not moved by the expansion of the insertion spring 111. The insertion spring 111 expands away from the rear face of the frame 112. Alternatively, the frame 112 may be formed as a flat plate to provide a reaction surface. Alternatively, the insertion spring 111 may be arranged in abutment with an inner surface of the housing 11.

The driving plunger 113 is formed having a cylindrical shape. A length of the driving plunger 113 is greater than a diameter of the driving plunger 113. The driving plunger 113 comprises a protruding part 115 at a point on the length of the cylinder. The driving plunger 113 comprises an angled surface 116 at one end of the cylinder. The angled surface 116 is at an angle with respect to the long axis of the cylinder. The angled end is called the front end of the driving plunger 113. The rear end of the cylinder, opposite to the angled surface 116, may be flat, that is, perpendicular to the long axis of the cylinder. The rear end of the cylinder may have rounded edges.

The driving plunger 113 is arranged at least partially within the insertion spring 111. An outer diameter of the cylindrical body of the driving plunger 113 is smaller than an inner diameter of the insertion spring 111. The driving plunger 113 is arranged co-axially with the insertion spring 111. The driving plunger 113 and insertion spring 111 are aligned on the second axis. The insertion spring 111 surrounds a rear portion of the driving plunger 113, including the rear end of the driving plunger 113.

The protruding part 115 extends radially outwards to engage with the insertion spring 111. The diameter of the protruding part 115 is greater than that of the insertion spring 111. The insertion spring 111 abuts against a rear face of the protruding part 115. The insertion spring 111 surrounds a rear portion of the driving plunger 113 between the protruding part 115 and the rear end of the driving plunger. The insertion spring 111 pushes against the protruding part 115 as it expands. The insertion spring 111 can move the driving plunger 113 along the second axis as it expands.

Alternatively, the diameter of the insertion spring 111 may be smaller than that of the driving plunger 113. The insertion spring may engage with the rear face of the driving plunger 113. The rear face of the driving plunger 113 may have a groove or recess to engage with the insertion spring 111. Further alternatively, the driving plunger 113 may comprise a cavity which is open at a rear end of the driving plunger 113. The insertion spring 111 may be arranged within the cavity of the driving plunger 113.

The insertion spring latch 114 is configured to retain the insertion spring 111 in the fully compressed state and to release the insertion spring 111 when the driving mechanism 110 is activated. The insertion spring latch 114 comprises one or more latching elements arranged in the opening of the frame 112. The insertion spring latch 114 has a first latched state and a second unlatched state.

In the latched state, the one or more latching elements of the insertion spring latch 114 are arranged in a forward position with respect to the protruding part 115 of the driving plunger 113. The insertion spring latch 114 engages with a forward face of the protruding part 115. The insertion spring latch 114 is fixedly attached to the frame 112. The insertion spring latch 114 is restrained from moving along the second axis. The insertion spring 111 pushes the driving plunger 113 against the insertion spring latch. The driving plunger 113 is restrained from moving along the second axis by the insertion spring latch. The insertion spring latch 114 retains the insertion spring 111 within the frame 112.

In the unlatched state, the one or more latching elements of the insertion spring latch 114 are disengaged from the protruding part 115. The insertion spring latch 114 is moved radially away from the second axis. The insertion spring latch 114 is moved away from the driving plunger 113 towards the frame 112. The driving plunger 113 can be moved along the second axis past the insertion spring latch 114. The insertion spring 111 can push against the rear face of the protruding part 115 and move the driving plunger 113 along the second axis.

The insertion spring latch 114 can be operated to move between the latched state and the unlatched state. The insertion spring latch 114 can be operated to move from the latched state to the unlatched state when the insertion mechanism 100 is activated.

The insertion spring latch 114 may alternatively be engaged with the insertion spring 111 in the latched state. The insertion spring 111 may abut with the one or more latching elements of the insertion spring latch 114. The protruding part 115 may be arranged in a forward position of the insertion spring latch 114 along the second axis. In the unlatched state the insertion spring latch 114 may allow the insertion spring 111 to expand along the second axis and engage with the protruding part 115.

The angled surface 116 of the driving plunger 113 is configured to engage with the cam 120. The angled surface 116 is formed at an angle of about 45 degrees with respect to the second axis. The angled surface 116 forms an angle of about 45 degrees with the lower side 11b of the case 11. The angle of the angled surface 116 relative to the lower side 11b may be between about 20 degrees and about 50 degrees. A width of the driving plunger 113 may be enlarged at a forward end to increase the size of the angled surface 116. The angled surface 116 may be truncated at a forward end by a flat portion, that is, a surface which is perpendicular to the second axis.

The cam 120 comprises an angled surface 121 and a guide 122. The cam 120 is formed as a triangular body. The angled surface 121 is angled between the first axis and the second axis. A lower face of the cam 120 is perpendicular to the first axis. A forward face of the cam is perpendicular to the second axis. The cam 120 is triangular in cross-section. The cam 120 may be a triangular prism having a constant cross-section. Alternatively, the cam 120 may be formed with any shape including the angled surface 121.

The angled surface 121 is formed at an angle of about 45 degrees with respect to the second axis. The angled surface 121 forms an angle of about 45 degrees with the lower side 11b of the case 11. The angle of the angled surface 121 relative to the lower side 11b may be between about 20 degrees and about 50 degrees. The angle of the angled surface 121 may be any angle which corresponds to the angled surface 116 of the driving plunger 113. The angles of the angled surface 116 and the angled surface 121 add up to 90 degrees. The driving plunger 113 is perpendicular to the first axis when the angled surface 116 is engaged with the angled surface 121. Alternatively, the angled surfaces may not add up to 90 degrees if the driving mechanism 110 is arranged at an angle within the housing of the device 10.

The angled surface 121 of the cam 120 is longer in cross section than the angled surface 116. The angled surface 116 of the driving plunger 113 can move across the angled surface 121. Alternatively, the angled surface 116 may be longer than the angled surface 121, or the surfaces may have the same length.

The guide 122 is configured to allow movement of the cam 120 along the first axis only. The guide 122 comprises one or more rails extending along the first axis, and corresponding grooves in the body of the cam 120. Alternatively, the guide 122 may include a rail passing through an opening in the body of the cam 120. Further alternatively, the guide 122 may comprise a retaining element in abutment with the forward face of the body of the cam 120 to prevent movement along the second axis.

The cam 120 is coupled to the needle 12. The needle 12 extends downwards from the cam 120 along the first axis. The needle 12 may extend out of a lower face of the body of the cam 120. The body of the cam 120 may be formed around an upper end of the needle 12. Alternatively, the needle may be arranged on an end face of the cam 120. The needle 12 may be fixedly attached to an end face of the cam 120, for example, using an adhesive.

The needle 12 is configured to move with the cam 120. The cam 120 is configured to move the needle 12 along the first axis. The first axis is the longitudinal axis of the needle 12. The first axis is perpendicular to the lower side 11b of the housing 11. As the cam 120 moves along guide 122 in the direction of the first axis, the needle is moved along the first axis.

FIG. 1 shows the device 10 in an initial state. The needle 12 is in the retracted position. The needle 12 is entirely within the housing 11 of the device 10. The aperture 14 may include a seal or septum to cover the aperture 14 in the initial state and seal the interior of the housing 11. The insertion spring 111 is fully compressed in the initial state. The insertion spring latch 114 is in the latched state. The insertion spring latch 114 is engaged with the protruding part 115. The insertion spring latch 114 prevents the driving plunger 113 from movement along the second axis. The protruding part 115 retains the insertion spring 111 in the compressed state. The insertion spring 111 is retained entirely within the frame 112. The insertion spring 111 is prevented from expanding along the second axis by the protruding part 115 and the insertion spring latch 114. Alternatively, the insertion spring latch 114 may be engaged directly with the insertion spring 111, as described above.

In the initial state, the driving plunger 113 is engaged with the cam 120. The angled surface 116 is in abutment with the angled surface 121. The driving mechanism 100 is aligned with the second axis of the device 10. The angled surface 116 is parallel to the angled surface 121. The driving plunger 113 is arranged such that movement along the second axis results in the driving plunger applying a force to the cam 120 along the second axis. The driving plunger 113 is configured to apply a force to the cam 120 along the second axis when the driving mechanism 110 is activated.

FIG. 2 shows the device 10 in an engaged state. The insertion mechanism 100 has been activated. The insertion spring 111 is in an activated state. The needle 12 is in the engaged position. The device 10 is ready to begin the medicament administration process.

The insertion mechanism 100 may be activated by, for example, a switch arranged to be pressed by the patient or care giver. The switch may be mechanical or may be electronic. An electronic switch may provide a signal to a controller which controls the activation of the insertion mechanism 100. Alternatively, a controller may control the insertion mechanism 100 automatically, in response to detecting that the device 10 has been placed in position on the patient's skin. The insertion mechanism 100 may be prevented from activating unless the device 10 is placed in position on the patient's skin.

Activation of the insertion mechanism 100 causes the insertion spring latch 114 to release the insertion spring 111. The insertion spring latch 114 is moved from the latched state to the unlatched state. The insertion spring latch 114 allows the protruding part 115 to pass the insertion spring latch 114 along the second axis. The insertion spring 111 applies a force along the second axis to the protruding part 115 of the driving plunger 113. The driving plunger 113 is caused to move along the second axis by the insertion spring 111. The insertion spring 111 expands along the second axis until fully extended in the activated state. The insertion spring 111 moves from the initial state to the activated state.

The driving mechanism 110 applies a force to the cam 120 when activated. Movement of the driving plunger 113 along the second axis causes the angled surface 116 to apply a force along the second axis to the angled surface 121 of the cam 120. The angle of the interface between the driving plunger 113 and the cam 120 causes a component of the force at the angled surface 121 to be directed along the first axis. The cam 120 is restricted from moving along the second axis by the guide 122. The cam 120 and the needle 12 are caused to move along the first axis towards the lower side 11b of the case 11.

The cam 120 is configured to move along a first axis in response to a force along a second axis. The cam 120 can translate motion along the second axis to motion along the first axis. The second axis is perpendicular to the first axis. The cam 120 is configured to move along the first axis in response to the force applied by the driving plunger 113. The cam 120 is arranged to receive a force along the second axis at the angled surface 121. A component of the force at the angled surface 121 is directed along the first axis and causes movement of the cam 120 along the first axis.

The angled surface 116 moves across the angled surface 121. Where the angled surface 121 is angled at 45 degrees to the second axis, a displacement of the driving plunger 113 along the second axis causes the same displacement of the cam 120 along the first axis. The needle 12 can be moved to the engaged position by movement of the cam 120 along the first axis. The needle 12 moves through the aperture 14 into the engaged position. The needle 12 may piece or rupture a seal covering the aperture 14 as it moved through the aperture 14 into the engaged position.

The cam 120 of the device 10 allows the driving mechanism 110 to be mounted sideways within the device 10. The driving mechanism 110 is longest in the direction along which it applies a force. By mounting the driving mechanism 110 sideways, with the longest axis parallel to the contact surface 11*b* of the device 10, a medicament delivery device 10 with a smaller vertical extent can be provided. The device 10 is formed to have a large contact surface 11*b* and a small vertical extent between the lower side 11*b* and the upper side 11*a* of the housing 11. The device 10 is stable when held against the patient's skin during a medicament administration process. The device 10 can be held securely and minimises rocking which could change the insertion angle of the needle 12. The needle 12 can be inserted perpendicular to the patient's skin and maintained in position during the medicament administration process. The increased area of the contact surface 11 provides a greater amount of friction and minimises slippage which could move the needle 12 laterally. The device 10 improves patient comfort and improves ease of use.

The injection mechanism 200 is shown in an initial state in FIG. 1 and FIG. 2. The injection mechanism 200 is configured to deliver medicament through the needle 12 when activated. The medicament is provided in the syringe 13. The syringe 13 comprises a medicament chamber 15 and a stopper 16. The medicament chamber 15 is generally cylindrical, with an opening at each end. The medicament chamber 15 may be formed of glass or a plastic material.

The stopper 16 is arranged within the medicament chamber 15. The stopper 16 forms a tight seal with the walls of the medicament chamber 16. The stopper 16 may be, for example, rubber or a synthetic rubber-like material. Alternatively, the stopper 16 may have the form of a plunger which passed through the opening and has an external component. When the injection mechanism 200 is in the initial state, the stopper 16 is disposed at one end of the medicament chamber 15.

A conduit 17 connects the medicament chamber 15 with the needle 12. The conduit 17 may be, for example, a flexible pipe or hose. One end of the conduit 17 is connected to an opening of the medicament chamber 15. The conduit 17 is connected to the end of the medicament chamber 15 which lies furthest from the needle 12. The other end of the conduit 17 is connected to the needle 12. The conduit 17 is connected to an upper end of the needle 12.

A portion of the length of the needle 12 is deflected at a right angle with respect to the first axis. The deflected portion of the needle 12 is disposed at an upper end of the needle 12 configured to receive medicament from the syringe 13. The needle 12 is configured to receive medicament through the conduit 17.

The injection mechanism 200 comprises an injection spring 211, an injection spring latch 212 and a syringe plunger 213. When activated, the injection spring 211 is configured to expand. The injection spring 211 is arranged to push the syringe plunger 213 through the medicament chamber 15 when activated.

The injection spring 211 is a compressible spring, for example, an extended coil spring. In an initial state, the injection spring 211 is fully compressed. In an activated state, the injection spring 211 is fully extended.

FIG. 2 shows the device 10 in the engaged state, ready to begin the medicament administration process. The injection spring 211 is in the initial state and is fully compressed. The injection spring latch 212 is configured to retain the injection spring 211 in the fully compressed state and to release the injection spring 211 when the injection mechanism 200 is activated. When the injection spring latch 212 releases the injection spring 211, the injection spring 211 can expand until the injection spring 211 is fully extended in the activated state.

The syringe plunger 213 comprises a protruding part 215 at a point on the length of the cylinder. The protruding part 215 extends radially outwards to engage with the injection spring 211. The injection spring 211 pushes against the protruding part 215 as it expands to move the syringe plunger 213 through the medicament chamber 15. The injection spring latch 212 may be engaged with the protruding part 215 in the initial state, to retain the injection spring 211 in the compressed state. Alternatively, the injection spring latch 212 may be engaged directly with the injection spring 211.

The syringe plunger 213 is arranged to be pushed through the medicament chamber 15 by the injection spring 211. The syringe plunger 213 is formed as a cylinder extending co-axially with the injection spring 211 and extending through the injection spring 211. One end of the syringe plunger 213 is disposed within the medicament chamber 15. The syringe plunger 213 extends through an opening of the medicament chamber 15. The syringe plunger 213 forms a tight seal with the opening to prevent the medicament from exiting the medicament chamber 15. Alternatively, the syringe plunger 213 may engage with the stopper 16 of the medicament chamber 15 outside the medicament chamber 15.

The syringe plunger 213 is coupled to the stopper 16. The syringe plunger 213 is arranged to move the stopper 16 from one end of the medicament chamber 15 to the other end as the syringe plunger 215 is pushed through the medicament chamber 15. The syringe plunger 213 is configured to move the stopper 16 through the medicament chamber 15 when the injection mechanism 200 is activated.

FIG. 3 shows the device 10 in the process of administering the medicament. The injection mechanism 200 has been activated. The injection spring 211 is partially extended, and is moving towards the activated state.

Activation of the injection mechanism 200 causes the stopper 16 to move towards the other end of the medicament chamber 15, causing medicament to be ejected from the medicament chamber through the opening at the other end of the medicament chamber 15.

The injection mechanism 200 may be activated by, for example, a switch arranged to be pressed by the patient or care giver. The switch may be mechanical or may be electronic. An electronic switch may provide a signal to a controller which controls the activation of the injection mechanism 200. Alternatively, a controller may control the injection mechanism 200 automatically, after the needle 12 has been moved to the engaged position.

Activation of the injection mechanism 200 causes the injection spring latch 212 to release the injection spring 211.

The injection spring 211 moves from the initial state to the activated state. The injection spring 211 expands until fully extended in the activated state. The injection spring 211 applies a force to the protruding part 215 of the syringe plunger 213. The syringe plunger 213 is caused to move through the medicament chamber 15 by the insertion spring 211.

Movement of the syringe plunger 213 through the medicament chamber 15 causes the stopper 16 to move from one end of the medicament chamber 15 to the other end. Medicament is expelled from the medicament chamber 15 through the conduit 17 by the stopper 16. The medicament is delivered to the needle 12 through the conduit 17 and is delivered to the patient through the needle 12.

Figure 4:
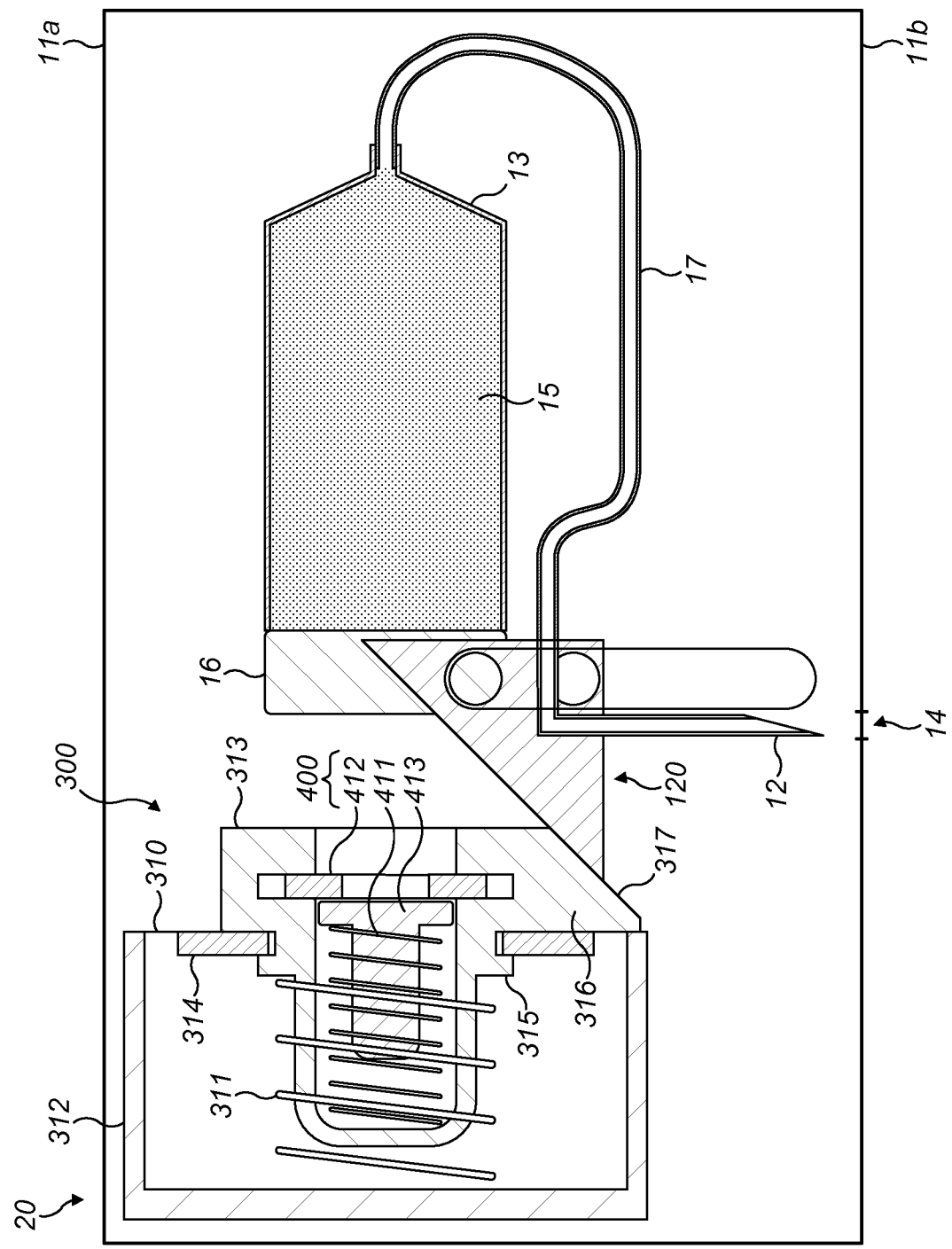
FIG. 4 is a schematic side view of a second embodiment of a medicament delivery device.
Figure 5:
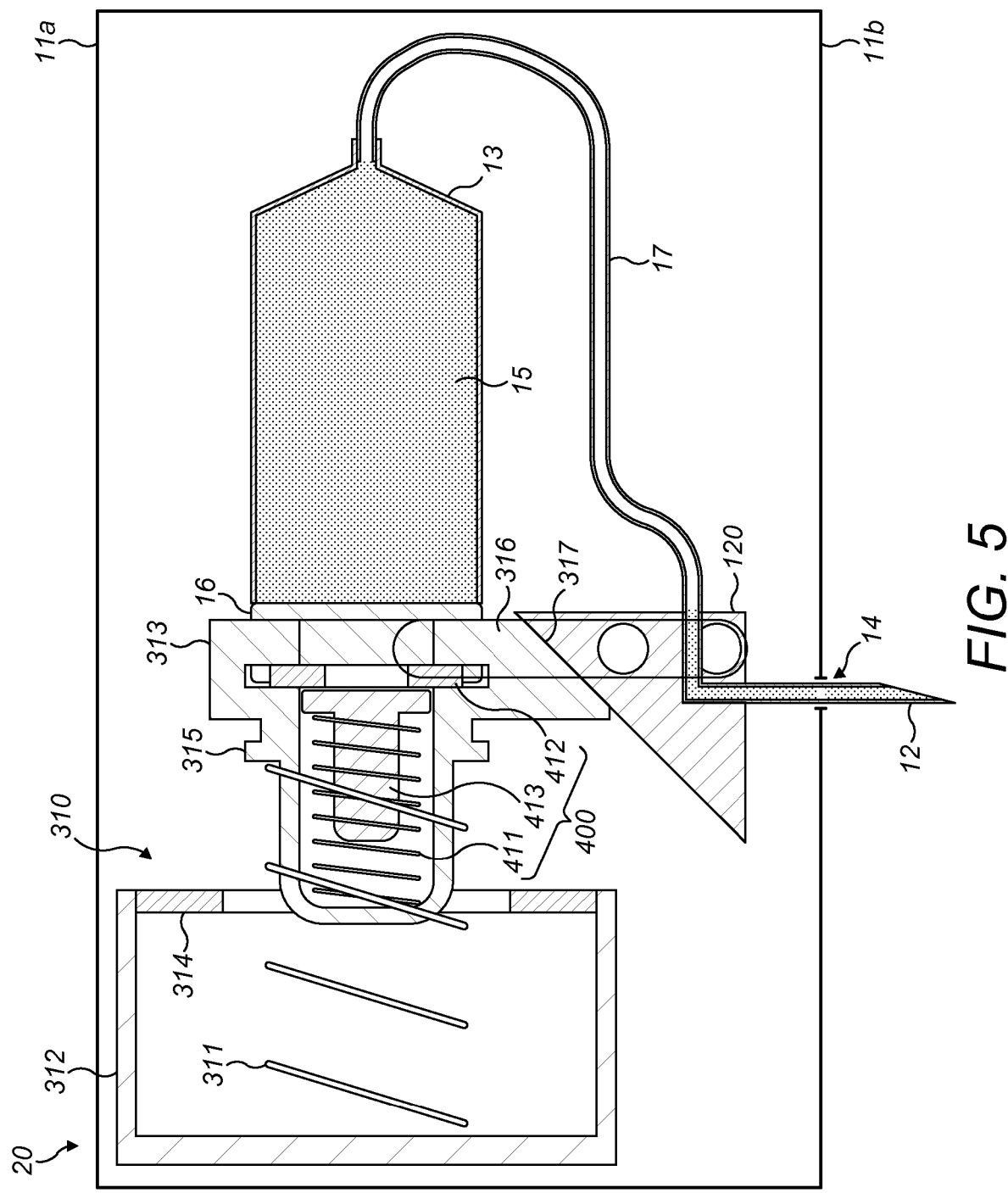
FIG. 5 is a schematic side view of the FIG. 4 injection device.
Figure 6:
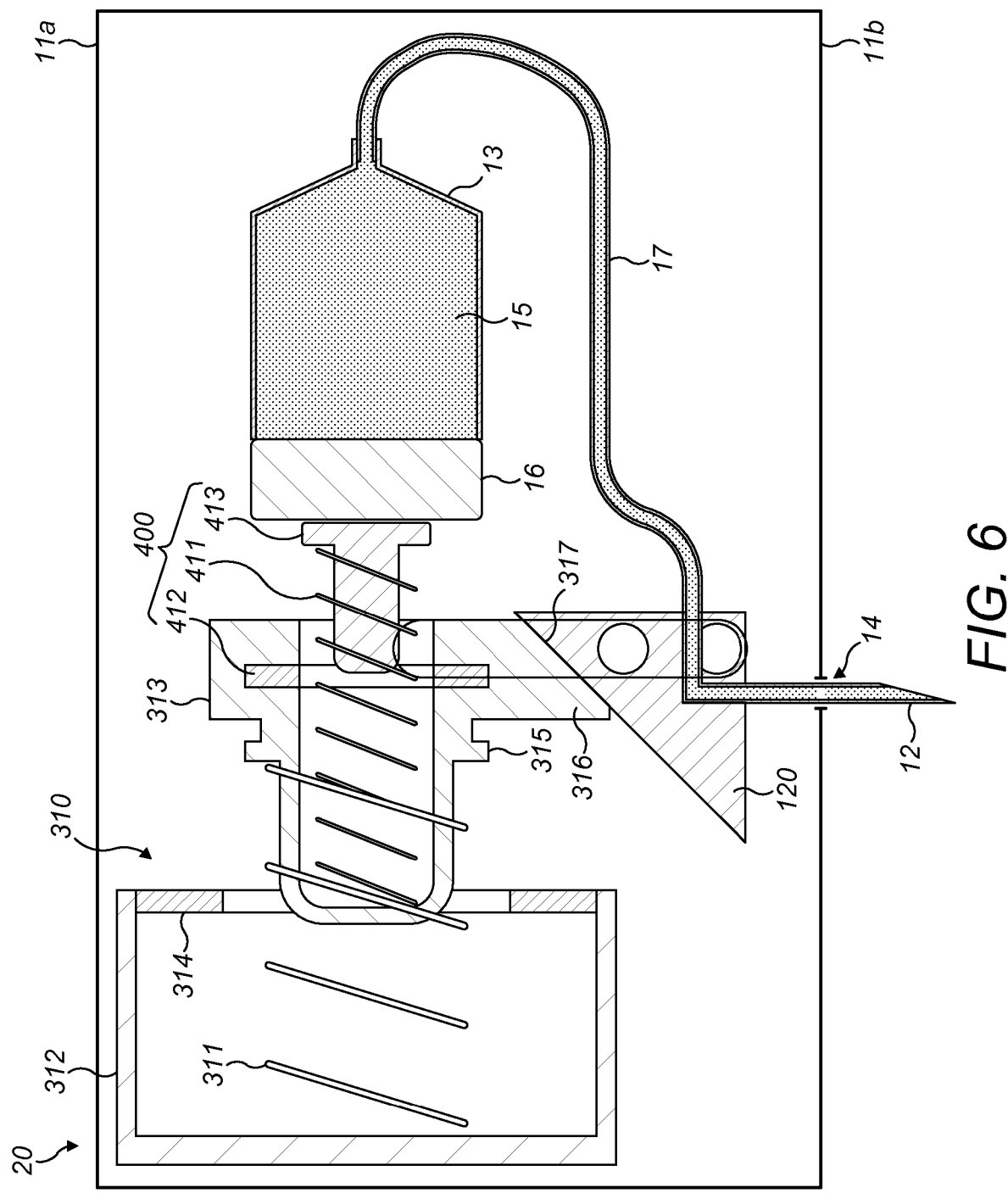
FIG. 6 is a schematic side view of the FIG. 4 injection device.

FIGS. 4 to 6 show a second embodiment of a medicament delivery device 20. The device 20 comprises a needle insertion mechanism 300 and a medicament injection mechanism 400. Other elements not described are substantially as described with respect to the first embodiment.

The needle insertion mechanism 300 is configured to move the needle 12 from the retracted position to the engaged position. The needle insertion mechanism 300 comprises a driving mechanism 310 configured to engage with the cam 120.

The driving mechanism 310 comprises an insertion spring 311, a frame 312 and an insertion spring latch 314, substantially as described with respect to the first embodiment. The driving mechanism 310 further comprises a driving plunger 313. The driving plunger 313 is formed having a cylindrical shape. The driving plunger 313 is aligned co-axially with the insertion spring 311 along the second axis. The driving plunger 313 comprises a protruding part 315 for engaging with the insertion spring 311, as described above with respect to the first embodiment. The insertion spring 311 surrounds a rear portion of the driving plunger 313 between a rear end and the protruding part 315.

The driving plunger 313 is configured to house the injection mechanism 400 in an initial state of the device 10. The driving plunger 313 is formed as a hollow cylinder. The driving plunger 313 includes an opening at one end. The forward end of the driving plunger 313, which is furthest from the insertion spring 313 is, open and the hollow interior of the cylinder is exposed. The injection mechanism 400 can be arranged in the interior of the driving plunger 313. An inner diameter of the driving plunger 313 is greater than an outer diameter of the injection mechanism.

The driving plunger 313 further comprises a cam engaging part 316. The cam engaging part 316 extends outwards from the cylindrical portion of the driving plunger 313. The cam engaging part 316 is integrally formed with the cylindrical portion. The cam engaging part extends from a forward end of the cylindrical part, which is adjacent to the opening. The cam engaging part 216 extends downwards, in the direction of the first axis.

The cam engaging part 316 is formed having a rectangular shape. The cam engaging part 316 comprises an angled surface 317. A lower face of the cam engaging part 316, furthest from the cylindrical portion of the driving plunger 313, is formed at an angle. The angled surface 317 corresponds to the angled surface 121 of the cam 120, in the same way as the angled surface 116.

The injection mechanism 400 comprises an injection spring 411, an injection spring latch 412 and a syringe plunger 413, substantially as described with respect to the first embodiment above. The outer diameters of the injection spring 411 and the syringe plunger 413 are smaller than the inner diameter of the driving plunger 313. A length of the injection spring 411 when fully compressed is shorter than a length of the interior of the driving plunger 313.

The injection spring latch 412 is configured to retain the injection spring 411 in the fully compressed state and to release the injection spring 411 when the injection mechanism 400 is activated. The injection spring latch 412 is disposed within the cylindrical walls of the driving plunger 313, to retain the injection spring 411 within the driving plunger 313. The injection spring latch 412 comprises one or more latching elements disposed in the walls of the driving plunger 313. The injection spring latch 412 is arranged adjacent to the opening of the driving plunger 313. The driving plunger 313 may include an enlarged portion with thicker cylindrical walls which accommodate the injection spring latch 412. The injection spring latch 412 has a first latched state and a second unlatched state.

In the latched state, the one or more latching elements of the injection spring latch 412 are arranged in a forward position with respect to a protruding part 415 of the syringe plunger 413. The injection spring latch 412 engages with a forward face of the protruding part 415. The injection spring latch 412 is fixedly attached to the driving plunger 313. The injection spring latch 412 is restrained from moving along the second axis. The injection spring 411 pushes the syringe plunger 413 against the injection spring latch 412. The syringe plunger 413 is restrained from moving along the second axis by the injection spring latch 412. The injection spring latch 412 retains the injection spring 411 within the driving plunger 313.

In the unlatched state, the one or more latching elements of the injection spring latch 412 are disengaged from the protruding part 415. The injection spring latch 412 is moved radially away from the second axis. The injection spring latch 412 is retracted within the wall of the driving plunger 313. The syringe plunger 413 can be moved along the second axis past the injection spring latch 412. When the injection spring latch 412 releases the injection spring 411, the injection spring 411 can push against the rear face of the protruding part 415 and move the syringe plunger 413 along the second axis.

The injection spring latch 412 can be operated to move between the latched state and the unlatched state. The injection spring latch 412 can be operated to move from the latched state to the unlatched state when the injection mechanism 400 is activated.

The injection spring latch 412 may alternatively be engaged with the injection spring 411 in the latched state. The injection spring 411 may abut with the one or more latching elements of the injection spring latch 412. The protruding part 415 may be arranged in a forward position of the injection spring latch 412 along the second axis. In the unlatched state the injection spring latch 412 may allow the injection spring 411 to expand along the second axis and engage with the protruding part 415.

FIG. 4 shows the device 20 in an initial state. The insertion spring 311 is in the initial state and is fully compressed within the frame 312. The insertion spring latch 314 is in the latched state. The insertion spring latch 314 is engaged with the protruding part 315 of the driving plunger 313. The insertion spring 311 is prevented from expanding along the second axis by the protruding part 315 and the insertion spring latch 314.

In the initial state the components of the injection mechanism 400 are housed within the driving plunger 313. The injection spring 411 is fully compressed, in an initial state. The injection spring latch 414 is in the latched state. The injection spring latch 414 is engaged with the protruding part 415 of the syringe plunger 413. The injection spring 411 is prevented from expanding along the second axis by the protruding part 415 and the injection spring latch 414. In the initial state, the injection mechanism 400 is separated from the syringe 13 by a distance along the second axis.

In the initial state, the driving plunger 313 is engaged with the cam 120. The cam engaging part 316 of the driving plunger 313 is in abutment with the cam 120. The angled surface 317 is in contact with the angled surface 121. The driving plunger 313 is arranged such that movement along the second axis results in the cam engaging part 316 applying a force to the cam 120 along the second axis. The driving plunger 313 is configured to apply a force to the cam 120 along the second axis when the driving mechanism 310 is activated.

FIG. 5 shows the device 10 in an engaged state. The insertion mechanism 300 has been activated. The insertion spring 311 is in an activated state. The needle 12 is in the engaged position. The device 10 is ready to begin the medicament administration process.

In the engaged state, the insertion spring latch 314 is moved from the latched state to the unlatched state. The insertion spring latch 314 allows the protruding part 315 to pass the insertion spring latch 314 along the second axis. The driving plunger 313 is caused to move along the second axis by the insertion spring 311. The cam engaging part 316 causes the cam 120 and the needle 12 to move along the first axis towards the lower side 11b of the case 11. The needle 12 moves through the aperture 14 into the engaged position.

The injection mechanism 400 is moved along the second axis with the driving plunger 313. The injection mechanism 400 is moved into abutment with the syringe 13. The syringe plunger 413 engages with the stopper 16 when the device 20 is in the engaged state. A forward face of the syringe plunger 413 is in abutment with the stopper 16. The syringe plunger 413 may pass through an opening of the medicament chamber 15 to engage with the stopper 16, or the stopper may include an external component for engaging with the syringe plunger 413.

The syringe plunger 413 is arranged such that further movement along the second axis exerts a force on the stopper 16 along the second axis. The syringe plunger 413 is configured to move the stopper 16 through the medicament chamber 15 when the injection mechanism 400 is activated. The driving mechanism 310 may include locking means or a ratchet mechanism configured to retain the driving plunger 313 in position after activation of the driving mechanism 310. The driving plunger 313 may provide a fixed reaction surface against which the injection spring 411 can push when the injection mechanism 400 is activated.

FIG. 6 shows the device 20 in the process of administering the medicament. The injection mechanism 400 has been activated. The injection spring 411 is partially extended, and is moving towards the activated state.

Activation of the injection mechanism 400 causes the injection spring latch 412 to release the injection spring 411. The injection spring latch 412 is moved from the latched state to the unlatched state. The injection spring latch 412 allows the protruding part 115 to pass the injection spring latch 412 along the second axis. The injection spring 411 moves from the initial state to the activated state. The injection spring 411 expands out of the driving plunger 313 and applies a force to the syringe plunger 413. The syringe plunger 413 is caused to move through the medicament chamber 15 by the insertion spring 411, causing the delivery of the medicament as described above.

The driving plunger 313 of the device 20 allows the injection mechanism 400 to be arranged within the driving mechanism 310. The nesting of components allows the device 20 to be contained within a smaller housing 11. A smaller device 20 is more convenient for the patient, as it is easier to handle and can be stored in a smaller space.

Figure 7A:
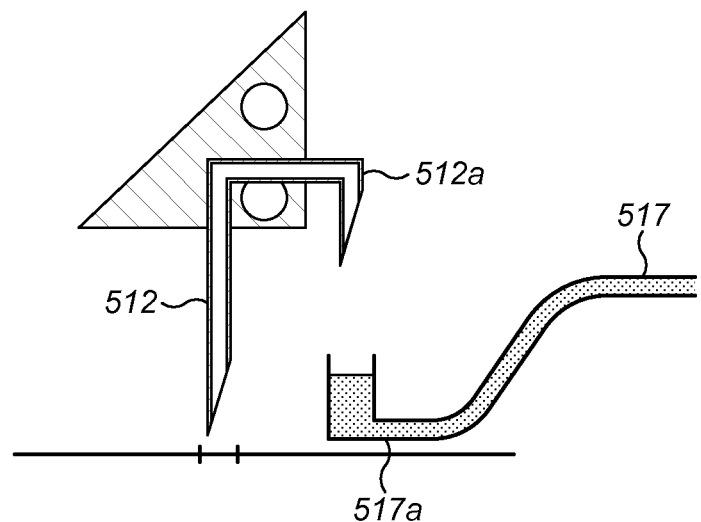
FIG. 7A is a partial schematic side view of a third embodiment of a medicament delivery device.
Figure 7B:
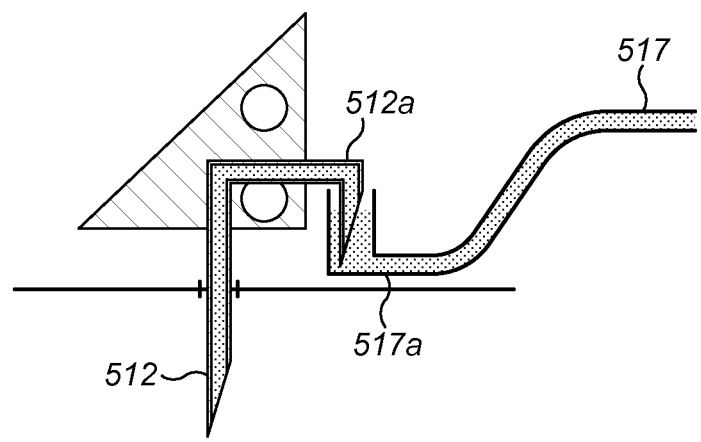
FIG. 7B is a partial schematic side view of the FIG. 7A device.

FIGS. 7A and 7B show an arrangement of a needle 512 and a conduit 517 according to a third embodiment of the device. The end of the conduit 517 is fixed in position. The needle 512 is configured to engage with the conduit 517 in the engaged position of the needle 512 only. Other elements not described are substantially as described with respect to the either of the first embodiment and the second embodiment.

The needle 512 comprises a piercing element 512a formed at an upper end. The deflected portion of the needle 512 is further deflected through a right angle so as to extend downwards along the first axis. Alternatively, the needle is formed to have a smooth curve through 180 degrees. The downward deflected portion of the needle 512 forms the piercing element 512a. The conduit 517 comprises a receiving portion 517a at an end furthest from the syringe 13. The receiving portion 517a is fixed in position. An upper face of the receiving portion 517a is formed having an opening which is initially sealed by, for example, a frangible seal or septum. The receiving portion 517a is arranged directly below the piercing element 512a along the first axis.

In the initial position of the needle 512, the piercing element 512a is separated from the receiving portion 517a along the first axis. As the needle 512 is moved into the engaged position, the piercing element 512a is caused to engage with the receiving portion 517a. The piercing element 512a pierces or ruptures the seal on the receiving portion 517a. In this way, the medicament can be delivered from the conduit 517 to the needle 512 in the engaged position.

Although a few embodiments of the present disclosure have been shown and described, it will be appreciated by those skilled in the art that changes may be made in these embodiments without departing from the invention, the scope of which is defined in the appended claims. Various components of different embodiments may be combined where the principles underlying the embodiments are compatible.

For example, the syringe of the second embodiment may be coupled to the driving plunger. The syringe may be configured to move with the driving plunger. The arrangement of the cam engaging part and the cam may be as described with respect to the second embodiment or, further alternatively, the cam engaging part may be formed on a forward end of the syringe. The cam may be arranged in a forward position with respect to the syringe. Coupled movement of the driving plunger and syringe may cause the cam engaging part to engage with the cam, as described above.

Where a spring has been described above, the insertion mechanism and the injection mechanism may be powered electrically or by a pneumatic or hydraulic drive mechanism. Alternatively, the device may be entirely user-driven.

The angled surface of the cam can be formed with a certain curvature, for example a scoop, to improve the performance of the insertion spring. Alternate cam mechanisms are also considered. For example, the cam may include a rotating part, wherein a force along the second axis causes the cam to rotate, which in turn causes a movement along the first axis.

Where the needle is described with a deflection, the needle may be straight along its entire length. The conduit may be a flexible tube coupled to an upper end of the needle. The device may include a plurality of needles coupled to the cam in any arrangement.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta-'decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A device for medicament delivery, the device comprising:
   a needle for delivering a medicament; and
   an insertion mechanism configured to urge the needle in a first direction parallel to a longitudinal axis of the needle, wherein the insertion mechanism comprises a driving mechanism which is configured to exert a force in a second direction perpendicular to the first direction,
   the insertion mechanism further comprising a cam which is coupled to the needle and is configured to receive the force from the driving mechanism and move in the first direction in response to the received force, wherein the driving mechanism comprises an insertion spring configured to expand in the second direction and a driving plunger having an angled surface to make contact with an angled surface of the cam and exert the force in the second direction on the cam upon expansion of the insertion spring; and
   an injection mechanism configured to urge a stopper of the device through a chamber of the device, wherein the injection mechanism comprises a second plunger and an injection spring, the second plunger being arranged to make contact with the stopper, the injection spring being configured to expand and push against the second plunger to urge the stopper through the chamber, and the injection spring being arranged coaxially within the insertion spring.

2. The device of claim 1, wherein the angled surface of the cam is arranged at an angle between the first direction and the second direction and a guide is configured to allow movement of the angled surface of the cam in the first direction only, and wherein the driving mechanism is configured to exert the force in the second direction on the angled surface of the cam.

3. The device of claim 2, wherein the angled surface of the cam is arranged at an angle between 20 degrees and 50 degrees with respect to the first direction.

4. The device of claim 1, wherein the driving mechanism comprises an insertion spring latch; and wherein:

in a first position, the insertion spring latch is arranged to prevent the insertion spring from expanding in the second direction; and in a second position, the insertion spring latch is arranged to allow the insertion spring to expand in the second direction.

5. The device of claim 1, further comprising:

a syringe for delivering the medicament through the needle, wherein the chamber comprises a medicament chamber of the syringe, and the second plunger comprises a syringe plunger.

6. The device of claim 5, wherein the injection mechanism comprises an injection spring latch; and wherein:

in a first position, the injection spring latch is arranged to prevent the injection spring from expanding; and in a second position, the injection spring latch is arranged to allow the injection spring to expand and push against the syringe plunger.

7. The device of claim 1, further comprising the medicament for delivery through the needle.

8. A device for medicament delivery, the device comprising:

a needle for delivering a medicament;

an insertion mechanism configured to urge the needle in a first direction parallel to a longitudinal axis of the needle, wherein the insertion mechanism comprises a driving mechanism which is configured to exert a force in a second direction perpendicular to the first direction;

the insertion mechanism further comprising a cam which is coupled to the needle and is configured to receive the force from the driving mechanism and move in the first direction in response to the received force, wherein the driving mechanism comprises a driving plunger having an angled surface to make contact with an angled surface of the cam and exert the force on the cam; and an injection mechanism configured to urge a stopper of the device through a chamber of the device, wherein the injection mechanism comprises a second plunger and an injection spring, the second plunger being arranged to make contact with the stopper, the injection spring being configured to expand and push against the second plunger to urge the stopper through the chamber, and wherein the injection spring, and the second plunger are arranged internally within the driving plunger, and the driving plunger is arranged such that, on expansion of the injection spring in the second direction, the second plunger is moved into contact with the stopper of the device.

9. The device of claim 8, wherein the device comprises a syringe configured to deliver the medicament through a flexible conduit, and the flexible conduit is connected with an upper end of the needle.

10. The device of claim 8, wherein the device comprises a syringe configured to deliver the medicament through a flexible conduit, and wherein the insertion mechanism is configured to move the needle in the first direction from a first position to a second position, wherein the needle in the first position is separated from the flexible conduit, and the needle in the second position is arranged to engage with the flexible conduit.

11. The device of claim 10, wherein the needle comprises a piercing element, and the piercing element of the needle is arranged to engage with a receiving portion of the flexible conduit in the second position.

* * * * *

UNITED STATES PATENT AND TRADEMARK OFFICE
CERTIFICATE OF CORRECTION

PATENT NO.         : 11,311,675 B2
APPLICATION NO.    : 16/324818
DATED              : April 26, 2022
INVENTOR(S)        : Michael Schabbach et al.

It is certified that error appears in the above-identified patent and that said Letters Patent is hereby corrected as shown below:

In the Claims

Column 20, Line 3, Claim 8, delete "medicament:" and insert -- medicament; --

Signed and Sealed this
Twenty-eighth Day of June, 2022

Katherine Kelly Vidal
*Director of the United States Patent and Trademark Office*